United States Patent [19]

Rea et al.

[11] 4,155,353

[45] May 22, 1979

[54] ELECTRODE AND METHOD FOR LARYNGEAL ELECTROMYOGRAPHY

[76] Inventors: James L. Rea; Jerry W. Templer; William E. Davis, all of 807 Stadium Rd., Columbia, Mo. 65201

[21] Appl. No.: 861,619

[22] Filed: Dec. 19, 1977

Related U.S. Application Data

[63] Continuation-in-part of Ser. No. 743,041, Nov. 18, 1976, abandoned.

[51] Int. Cl.² .............................................. A61B 5/04
[52] U.S. Cl. .................................... 128/642; 128/733
[58] Field of Search ............ 128/2.1 E, 2.06 E, 2.1 R, 128/2.1 M, 404, 418, 419 E, 419 P, 419 R, 422, DIG. 4

[56] References Cited

U.S. PATENT DOCUMENTS

| | | | |
|---|---|---|---|
| 3,057,356 | 10/1962 | Greatbatch | 128/422 |
| 3,212,496 | 10/1965 | Preston | 128/2.06 E |
| 3,313,293 | 4/1967 | Chesebrough et al. | 128/2.1 E |
| 3,543,761 | 12/1970 | Bradley | 128/418 X |
| 3,750,650 | 8/1973 | Ruttgers | 128/2.06 E |
| 3,804,080 | 4/1974 | Ruttgers et al. | 128/2.06 B |
| 3,826,244 | 7/1974 | Saleman et al. | 128/2.1 E |
| 3,971,364 | 7/1976 | Fletcher | 128/2.06 E X |

FOREIGN PATENT DOCUMENTS

| | | | |
|---|---|---|---|
| 4327686 | 11/1968 | Japan | 128/2.1 E |
| 283427 | 10/1970 | U.S.S.R. | 128/2.1 E |

OTHER PUBLICATIONS

Saleman et al., "A New Chronic . . . Microelectrode", The Int. Fed. for Med. & Bio. Eng., vol. 14, No. 1, p. 42-50, Jan. 1976.
Wise et al., "An Integrated . . . Microelectrodes", IEEE Trans. on Bio-Med. Eng., vol. 17, No. 3, Jul. 1970, pp. 238-247.

Primary Examiner—Lee S. Cohen
Attorney, Agent, or Firm—Fishburn, Gold & Litman

[57] ABSTRACT

An electrode for laryngeal electromyography comprises an insulator body having a pair of rigid conductors or posts mounted in a spaced apart relation therein. A pair of flexible electrical wires have one end connected with an associated post, and the other end adapted for connection to an electrical signal monitor. A tab projects outwardly of the insulator body, and is shaped for insertion into a laryngeal ventricle portion of the patient and prevents inadvertent removal of the electrode from a vocalis muscle thereof. The free ends of the posts are embedded into the patients vocalis muscle, and a signal generating probe is applied to surgically exposed internal tissue in the area surrounding the recurrent laryngeal nerve, whereby contact between the probe and the laryngeal nerve excites the vocalis muscle and the monitor, thereby indicating to the surgeon the exact location of the nerve.

15 Claims, 5 Drawing Figures

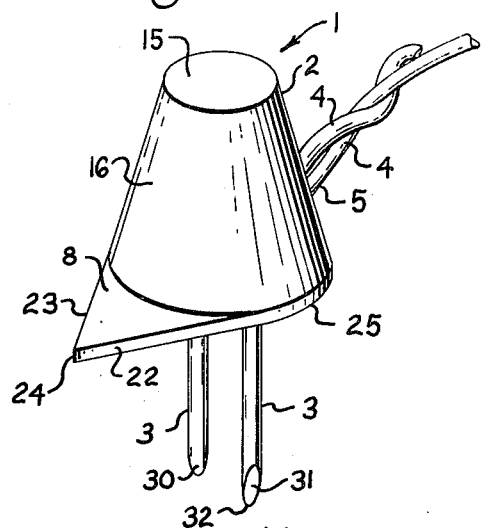
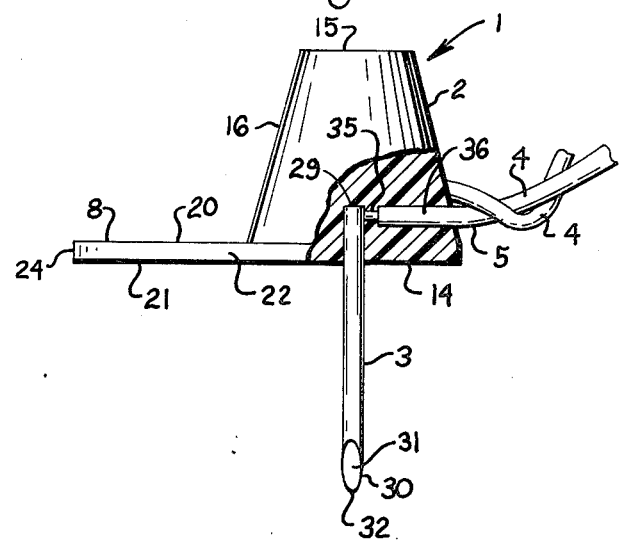
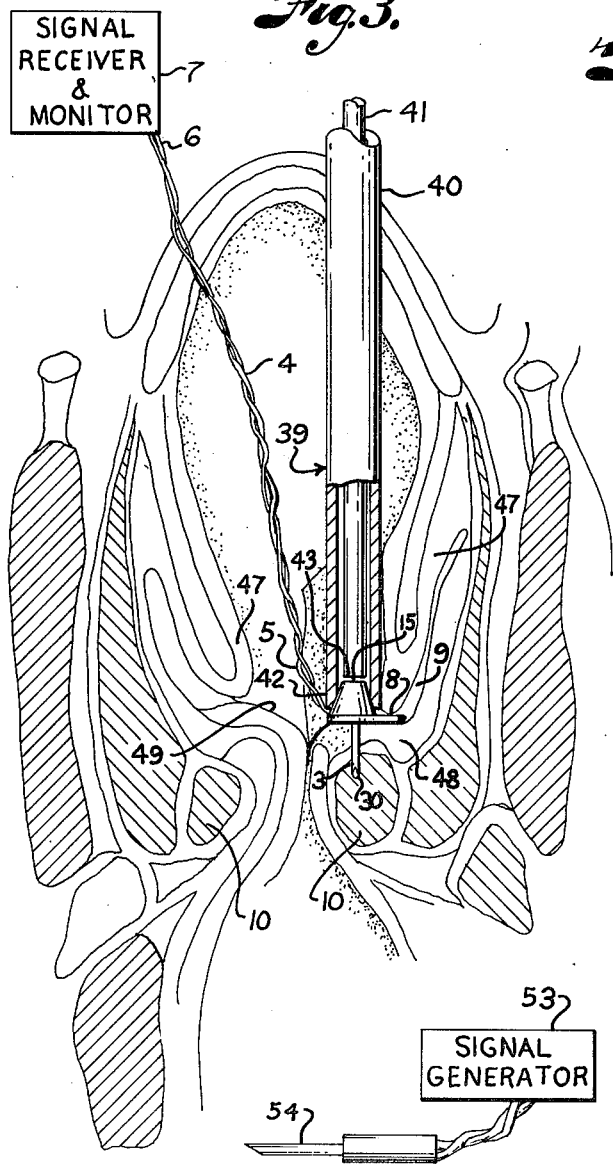
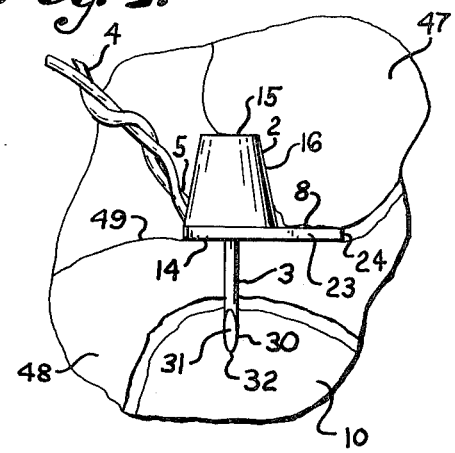
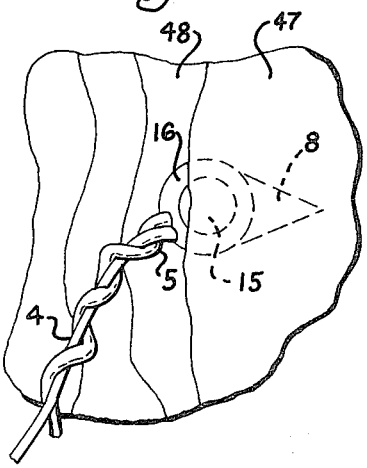

ELECTRODE AND METHOD FOR LARYNGEAL ELECTROMYOGRAPHY

This application is a continuation-in-part of our U.S. patent application Ser. No. 743,041, filed Nov. 18, 1976, now abandoned.

BACKGROUND OF THE INVENTION

This invention relates to electrodes, and in particular to an electrode and method for locating the recurrent laryngeal nerve in a surgery patient.

A quite serious and recurring problem for otolaryngologists is the post operative side effect of vocal cord paralysis following thyroid surgery. Even the best and most experienced surgeons, using the most sophisticated equipment heretofore available, encounter a substantial hazard that the recurrent laryngeal nerve (RLN) will be severed, stretched or bruised during surgery on or about the thyroid gland. This surgical hazard is a result of several factors, including the fact that the recurrent laryngeal nerve lies just posterior to the most inferior portion of the thyroid gland, and is very small and delicate. Further, it is quite difficult to distinguish this nerve from the background tissue when the area about the thyroid is inflamed, as well as covered with blood following the initial incision. As the result of these aforementioned complications, the risk of vocal cord damage following thyroid surgery is very high, and also is quite serious in that it can result in the patient's complete loss of speech. Even if the laryngeal nerve is simply been stretched or bruised, the loss of speech may last for several months. In the unfortunate cases where the nerve is completely severed, the paralysis is permanent, and surgical attempts to prepare the same have not yet proven successful.

The principal object of the present invention are: to provide an electrode and method for laryngeal electromyography to locate a recurrent laryngeal nerve; to provide such an electrode and method for continuous, intraoperative laryngeal nerve location during thyroid surgery; to provide such an electrode and method which is easily inserted in the patient and adapted for reliable operation; to provide such an electrode and method which is simply and accurate in operation whereby surgeons without extensive experience in thyroid surgery may conduct said surgery, yet avoid damage to the laryngeal nerve; to provide such an electrode having an insulator body and tab connected therewith adapted for insertion into a laryngeal ventricle portion of the patient for preventing inadvertent removal of the electrode from the patient's vocalis muscle; to provide such an electrode and method including an audio monitor, whereby the location of the laryngeal nerve may be determined while the surgeon maintains continuous sight observation of the area of surgery; to provide such an electrode and method including an insertion device for accurately and securely placing the electrode in the patient's vocalis muscle without interfering with other equipment; and to provide such an electrode which is economical to manufacture, efficient in use, and particularly well adapted for the proposed use.

Other objects and advantages of this invention will become apparent from the following description taken in connection with the accompanying drawings wherein are set forth, by way of illustration and example, certain embodiments of this invention.

The drawings constitute a part of this specification and include exemplary embodiments of the present invention and illustrate various objects and features thereof.

FIG. 1 is a perspective view of an electrode embodying the present invention.

FIG. 2 is a side elevational view of the electrode with a portion thereof broken away to reveal internal construction.

FIG. 3 is a partially schematic view of a larynx portion of a patient, the electrode embedded therein, and an insertion device therefore, and illustrates a method for laryngeal electromyography embodying the present invention.

FIG. 4 is an enlarged, partially schematic, side elevational view of the electrode, and adjacent portions of the larynx as shown in FIG. 3.

FIG. 5 is an enlarged, partially schematic, top plan view of the electrode and associated larynx portions as shown in FIG. 3.

Referring more in detail to the drawings:

As required, detailed embodiments of the present invention are disclosed herein, however, it is to be understood that the disclosed embodiments are merely exemplary of the invention which may be embodied in various forms. Therefore, specific structural and functional details disclosed herein are not to be interpreted as limiting, but merely as a basis for the claims and is a representative basis for teaching one skilled in the art to variously employ the present invention and virtually any appropriately detailed structure.

The reference numeral 1 generally designates an electrode embodying the present invention and comprising an insulator body 2 having a pair of rigid conductors or posts 3 mounted in a spaced apart relation therein. A pair of flexible electrical conductors or wires 4 have one end thereof 5 connected with an associated post, and the other end 6 is adapted for connection to an electrical signal receiver and monitor 7. A tab 8 projects outwardly of the insulator body 2, and is shaped for insertion into a laryngeal ventricle portion 9 of the patient and prevents inadvertent removal of the electrode 1 from the vocalis muscle 10.

The insulator body 2 is constructed of a substantially rigid, electrically insulative material, such as a polyester or an other polymeric synthetic resin. The illustrated insulator body 2 has a frusto-conical shape with flat base and top surfaces 14 and 15 respectively, and an inclined side surface 16. For purposes of description herein, the terms "upper, lower, right, left, rear, front", and the like, shall relate to the electrode as oriented in FIG. 2, however, it is to be understood, that the electrode may assume virtually any alternative orientation without adversely effecting its operation. In this example, the base and top surfaces 14 and 15 have a diameter in the nature of 4 millimeters and 2.5 millimeters respectively, and the distance between these surfaces is approximately 4 millimeters. It has been determined that an electrode having the last noted dimension is particularly suited for the average patient, however, it is to be understood that various sizes of electrodes may be provided to accommodate all types of patients.

The insulator body 2 is preferably resistant to heat, so that the same may be autoclaved or otherwise sanitized, and is hard or rigid to facilitate grasping and insertion into the patient's larynx. The insulator is also preferably constructed of a material capable of detection by x-ray, whereby its presence and exact location in the patient's body can be readily ascertained.

The tab 8 is connected with the insulator body 2, projects outwardly thereof, and is shaped for insertion into the laryngeal ventricle portion 9 of the patient. The illustrated tab 8 is substantially flat, and includes an upper surface 20, and a lower surface 21 which is substantially coplanar with the base surface 14 of the insulator body 2. The tab 8 is constructed of a substantially rigid material such as synthetic resin, and is preferably integrally molded or otherwise formed with the insulator body 2. The tab 8 is positioned substantially perpendicularly with the respect to the central axis of the insulator body, and has a triangular shape formed by a pair of side edges 22 and 23 which converge to and intersect at an apex or free edge 24. The illustrated tab 8 forms a ridge 25 about the base surface 14 of the insulator body, and tab projects a distance in the nature of 3 millimeters outwardly of the base of the insulator body.

The posts 3 are rigid electrical conductors having an upper end 29 thereof fixedly mounted in a spaced apart relation in the insulator body 2. The posts 3 are securely connected with the insulative body by means of a press fit, bonding, or the like, and in the illustrated structure are molded therein, and have a thickness in the nature of 27 gauge. The posts 3 extend downwardly from the insulator body 2 in a substantially mutually parallel relation to a sharpened free end 30. The free ends 30 of each of the illustrated posts are shaped in an angle which extends downwardly from the outer surface of each post to the inner surface thereof, and forms a generally ovate shaped impaling surface 31 and leading edge 32. The impaling surfaces 31 face mutually outwardly in a diametrically opposed relation, and the posts 3 lay in a plane which is oriented substantially perpendicular to the plane passing through the tab apex 24 and the center of the insulator body. This relationship between the post impaling surfaces 31 and the tab provides for secure attachment of the electrode in the vocalis muscle 10. The posts 3 are preferably solid and have a substantially cylindrical configuration, and are constructed of a nonoxidizing material which has good electrical conductive characteristics, such as stainless steel, or the like. The illustrated posts 3 extend a distance in the nature of 5 millimeters from the base 14 for secure engagement with the vocalis muscle, and are spaced apart a distance in the nature of 2 millimeters measured center-to-center. The cylindrical portion of the posts may be coated with an antifriction material such as polytetra floroethylene or the like.

The flexible electrical conductors or wires 4 include a conductor core 35 and an insulative sheath or coating molded or otherwise axially fixed thereabout. The lower end 5 of each of the wires 4 is electrically connected with an associated one of the posts 3 at the upper end 29 of the post. The lower end 5 of each of the wires 4 is fixedly attached to the insulative body 2, and in the illustrated example, the wires 4 are frictionally engaged therein by molding the same at terminal wire segment 36 with the insulator body. The conductors 35 are very fine, in the nature of 40 gauge to facilitate threading the same into the patient's larynx. The wires are twisted about each other to alleviate the effect of spurious electromagnetic fields which might impinge thereon, and otherwise effect the received signal at the monitor 7. The illustrated wires 4 are connected to the insulator body at a point disposed diametrically opposite the tab 8, and a slightly spaced apart distance from the base surface 14 to facilitate insertion and retention of the electrode.

An insertion device 39 is provided to assist the user in quickly and accurately placing the electrode into the vocalis muscle 10 of the patient. The insertion device 39 comprises a cylinder 40 in which a rod member 41 is slidably mounted. The lower end 42 of the cylinder has a frustro-conically shaped interior surface which is adapted to mate with the side surface 16 of the electrode, and retain the same snuggly therein in a wedge-like fashion. The rod lower end 42 is adapted to abut the top surface 15 of the electrode and separate the insertion device 39 from the electrode after the same has been placed in the patient. The upper end of the insertion device includes a handle and trigger mechanism (not shown) which are connected to the cylinder 40 and rod 41 respectively for remotely manipulating the device. A resilient spring member (not shown) is mounted in the handle, and is adapted to retain the rod in a retracted position. The side wall of the cylinder 40 may be provided with a slot (not shown) adjacent the lower end 42 thereof to receive therein and accommodate the wires 4 during the insertion of the electrode.

The electrode 1 is particularly adapted for use in conjunction with a method for locating the recurrent laryngeal nerve in a thyroid surgery patient. The patient is first anesthesized, which typically includes the insertion of an intratracheal tube into the patient's mouth and into his trachea. The person who is to insert the electrode 1, such as the anesthesiologist, surgeon, or the like, then connects the electrode 1 with the lower end 42 of the insertion device 39 which retains the electrode therein. The electrode and insertion device unit are then inserted through the mouth of the patient and into the larynx area thereof. A laryngoscope is similarly placed into the patient, such that the person inserting the electrode, may accurately position the same. The electrode 1 is inserted into the vocalis muscle 10 associated with that side of the patient on which the thyroid surgery is to be performed. For example, in the arrangement illustrated in FIG. 3, the surgery is to be performed on the right side of the patient, and the electrode is therefore to be inserted into the right vocalis muscle 10.

The laryngeal ventricle portion 9 of the larynx into which the electrode 1 is to be positioned is a cavity which is formed by an upwardly positioned tissue termed the vestibular (ventricular) fold 47, and a downwardly oriented tissue 48 termed the vocalis or true vocal cord. The The vestibular fold 47 is a relatively soft and flexible tissue, whereas the true vocal cord 48 is relatively stiff or rigid and surrounds the vocalis muscle 10. The vestibular fold 47 generally drapes downwardly, and is abuttingly supported by the upper surface 49 of the true vocal cord 48, whereby the inserter of the electrode 1 uses the exterior surface of the cylinder 40 to displace the vestibular fold 47 inwardly and expose the laryngeal ventricle or sinus 9. As best illustrated in FIG. 4, the tab 8 is directed toward the interior of the laryngeal ventricle 9, and the posts 3 are inserted into the true vocal cord, whereby the post free ends are in abutting contact with the vocalis muscle 10. In the illustrated example, the entire impaling surface 31 of each of the posts is disposed wholly within the vocalis muscle 10. The operator then extends the rod 41 and separates the electrode 1 from the insertion device 39, and carefully withdraws the insertion device from the patient. As the insertion device 39 is withdrawn, the vestibular fold 47 reforms from its formerly distorted position, about the electrode, with the same resting on the upper surface of the tab, and the top surface 15 of the insulator body. This action securely retains the electrode in the proper position within the laryngeal ventricle. The spaced apart posts 3 prevent the electrode from rotating out of position.

The upper ends 6 of each of the wires 4 are connected with the signal receiver and monitor 7 which is positioned at a convenient location adjacent the surgery site. The signal receiver and monitor comprises a device which will receive an electrical signal originating in the vocalis muscle 10 and transmitted thereto through the wires 4, and provide a display of the signal. The signal receiver and monitor may comprise an oscilloscope or the like, and is preferably a mechanism which provides an audible alarm upon receipt of the electrical signal, whereby the location of the recurrent laryngeal nerve can be determined while the surgeon maintains continuous sight observation of the area of surgery.

A signal generator 53 includes a probe 54 and provides means for applying an electrical signal to the recurrent laryngeal nerve (not shown). The signal is of a relatively low voltage, in the nature of five volts, and is preferably a repetitive stimuli of low frequency, short pulses, in the nature of 4 to 30 pulses per seconds stimulation rate.

After the surgeon has made his initial incision, and is approaching the area of the recurrent laryngeal nerve, he simply applies the probe 54 to that area in which he believes the nerve to be located. If the probe contacts the laryngeal nerve, the signal applied thereto by the signal generator 53 is transmitted through the laryngeal nerve to the vocalis muscle 10 which is in turn thereby excited. Excitement of the vocalis muscle 10 causes an electrical impulse to be generated therein and is transmitted through the electrode posts 3 and wires 4 to the signal receiver and monitor 7. In the case of an audio monitor, the device shall emit popping sounds in a frequency which corresponds to the signal applied to the probe by the signal generator 53. Hence, the surgeon need only recognize the characteristic frequency of these popping sounds to know that he has located the recurrent laryngeal nerve. After having determined the location of the nerve, the surgeon can work very slowly and carefully in this area so as to insure the nerve is not injured. The electrode 1 may be removed from the patient by simply pulling on the wires 4 and threading the same back through the patients larynx and mouth.

It is to be understood that while we have illustrated and described certain form of our invention, it is not to be limited to the specific forms or arrangement herein described and shown.

We claim:

1. An electrode for laryngeal electromyography comprising:
   (a) an electrical insulator having a base, a top and a side;
   (b) a pair of rigid electrical conductors, each having a first end and a second end; said rigid conductors each having the first end thereof mounted in said insulator base and projecting outwardly therefrom in a mutually spaced apart relation, and including a cutting edge on the second end thereof for embedding the rigid conductors into a vocalis muscle of a patient;
   (c) a pair of flexible electrical conductors, each having a first end thereof connected with a different one of said rigid conductors, and including a second end thereof adapted for connection to a signal monitor; and
   (d) a tab connected with the insulator having a planar portion anatomically proportioned for insertion into a laryngeal ventricle portion of the patient and projecting outwardly of the insulator at an angle to said rigid conductors for preventing inadvertent removal of the electrode from the vocalis muscle.

2. An electrode as set forth in claim 1 wherein:
   (a) said insulator has a frustro-conical shape to facilitate insertion of said electrode.

3. An electrode as set forth in claim 1 wherein:
   (a) said rigid conductors depend substantially normally from said insulator base in a mutually parallel relation.

4. An electrode as set forth in claim 3 wherein:
   (a) said tab has flat opposed surfaces, and a triangular shape defined by tab side edges intersecting at an apex.

5. An electrode as set forth in claim 4 wherein:
   (a) said insulator base is substantially coplanar with a lower one of said tab opposed surfaces; and
   (b) said tab apex lies in a plane substantially perpendicular with a plane passing centrally through each of said rigid conductors.

6. An electrode as set forth in claim 1 wherein:
   (a) said first end of each of the flexible conductors is mounted in the insulator at a point therein disposed substantially opposite said tab.

7. An electrode as set forth in claim 1 wherein:
   (a) said tab is oriented substantially perpendicular to said rigid conductors.

8. An electrode as set forth in claim 1 wherein:
   (a) said tab has flat opposed surfaces, and a triangular shape defined by tab side edges intersecting at an apex.

9. An electrode as set forth in claim 8 wherein:
   (a) said insulator base is substantially coplanar with a lower one of said tab opposed surfaces.

10. An electrode as set forth in claim 9 wherein said rigid conductors each extend rectilinearly from the insulator.

11. An electrode as set forth in claim 8 wherein:
    (a) said tab apex lies in a plane substantially perpendicular with a plane passing centrally through each of said rigid conductors.

12. An electrode as set forth in claim 11 wherein:
    (a) said cutting edge on each of said rigid conductors comprises an impaling surface inclined downwardly from an outer surface of each rigid conductor to an inner surface thereof; said impaling surfaces facing mutually outwardly in a diametrically opposed relation, and each of said impaling surfaces being substantially perpendicular with said plane passing through said rigid conductors.

13. A method for locating a recurrent laryngeal nerve in a surgery patient comprising the steps of:
    (a) providing a laryngeal electrode having a pair of rigid electrical conductors mounted in an insulator, a pair of flexible conductors connected with the rigid conductors, and a tab projecting outwardly of the insulator;
    (b) guiding said electrode through a pharynx portion of said patient into a larynx portion thereof;
    (c) embedding a free end portion of each of said rigid conductors into a vocalis muscle portion of said larynx, and inserting the electrode tab into a laryngeal ventricle portion of said larynx to prevent inadvertent removal of the electrode from the vocalis muscle;

(d) connecting each of the flexible conductors with a monitor for sensing impulses in said vocalis muscle;

(e) providing a probe for exciting internal tissue in an area surrounding the laryngeal nerve and applying said probe thereto, whereby contact between the probe and the recurrent laryngeal nerve excites said vocalis muscle and said monitor thereby indicating the exact location of said nerve.

14. A method as set forth in claim 13 wherein:

(a) said electrode is detachably connected to an end of a tubular insertion tool to facilitate guiding and positioning said electrode.

15. A method as set forth in claim 13 wherein:

(a) said monitor provides an audible alarm whereby the location of said nerve is determined while maintaining continuous sight observation of said area of surgery.